(12) United States Patent
Copland (10) Patent No.: US 9,060,710 B2
(45) Date of Patent: Jun. 23, 2015

(54) SYSTEM AND METHOD FOR OCULAR TOMOGRAPHY USING PLENOPTIC IMAGING (71) Applicant: AMO Wavefront Sciences, LLC., Santa Ana, CA (US)

(72) Inventor: Richard J. Copland, Albuquerque, NM (US)

( * ) Notice: Subject to any disclaimer, the term of this patent is extended or adjusted under 35 U.S.C. 154(b) by 50 days.

(21) Appl. No.: 13/829,317

(22) Filed: Mar. 14, 2013

(65) Prior Publication Data
US 2014/0268041 A1  Sep. 18, 2014

(51) Int. Cl.
*A61B 3/14* (2006.01)
*A61B 3/00* (2006.01)
*A61B 3/10* (2006.01)

(52) U.S. Cl.
CPC ...................... *A61B 3/102* (2013.01)

(58) Field of Classification Search
CPC ............ A61B 3/14; A61B 3/12; A61B 3/103; A61B 3/152; A61B 3/113; A61B 3/1208; A61B 3/1225; A61B 3/024; A61B 3/032; A61B 3/1015
USPC ................. 351/206, 200, 205, 208–210, 218, 351/221–223, 246, 211
See application file for complete search history.

(56) References Cited

U.S. PATENT DOCUMENTS

| | | | |
|---|---|---|---|
| 4,665,913 A | 5/1987 | L'esperance, Jr. | |
| 4,669,466 A | 6/1987 | L'esperance | |
| 4,732,148 A | 3/1988 | L'esperance, Jr. | |
| 4,764,930 A | 8/1988 | Bille et al. | |
| 4,770,172 A | 9/1988 | L'esperance, Jr. | |
| 4,773,414 A | 9/1988 | L'esperance, Jr. | |
| 5,108,388 A | 4/1992 | Trokel | |
| 5,163,934 A | 11/1992 | Munnerlyn | |
| 5,207,668 A | 5/1993 | L'esperance, Jr. | |
| 5,219,343 A | 6/1993 | L'esperance, Jr. | |
| 5,646,791 A | 7/1997 | Glockler | |
| 5,993,438 A | 11/1999 | Juhasz et al. | |
| 7,931,371 B2 | 4/2011 | Dai | |
| 2010/0004537 A1* | 1/2010 | Eilers et al. ................... | 600/443 |
| 2011/0080561 A1* | 4/2011 | Hayashi et al. ................ | 351/206 |
| 2011/0234977 A1* | 9/2011 | Verdooner .................... | 351/207 |
| 2012/0069298 A1* | 3/2012 | Ng ................................ | 351/206 |
| 2013/0010260 A1* | 1/2013 | Tumlinson et al. ........... | 351/206 |

* cited by examiner

*Primary Examiner* — Dawayne A Pinkney (57) ABSTRACT

Improved systems and methods for ocular tomography are provided. These systems and methods can be used to improve the effectiveness of a wide variety of different ophthalmic diagnostic procedures, and various surgical and non-surgical treatments. One embodiment provides a system and method for determining ocular tomography data for the eye using a plenoptic detector. For example, an ocular tomography system can comprise a set of light sources configured to illuminate an eye, a plenoptic detector configured to receive images of the light sources reflected from surfaces of the eye and generate plenoptic image data representing the images, and a processing system coupled to the plenoptic detector. The processing system is configured to analyze the plenoptic image data to determine tomography data for the eye.

16 Claims, 6 Drawing Sheets

SYSTEM AND METHOD FOR OCULAR TOMOGRAPHY USING PLENOPTIC IMAGING

TECHNICAL FIELD

Embodiments of the present invention generally relate to vision techniques, and particularly to techniques for ocular tomography.

BACKGROUND OF THE INVENTION

Many modern ophthalmic surgical procedures require accurate measurements of the eye. For example, measurements of aberrations of the eye are important for the diagnosis and treatment of visual defects and acuity. Furthermore, there are a growing number of ways that aberrations can be corrected using both surgical and non-surgical means. Many of these methods rely on accurate, precise measurements of the whole ocular system so that patients may be screened, the corrective means applied and tested, and follow up care provided as appropriate.

One type of ocular measurement is generally referred to as ocular tomography. In general, ocular tomography is the measurement of the three-dimensional structure of the ocular system. For example, ocular tomography can include the determination of the thicknesses and/or radii of the cornea and lens. Ocular tomography can also include the determination of the distance between the lens and the cornea. Each of these measurements can be useful in various surgical and non-surgical treatments, and improved accuracy and precision of these measurements may lead to improved methods for correcting visual defects, and for identifying patients in need of care.

For these and other reasons there a continuing need for improved ocular tomography techniques.

BRIEF SUMMARY OF THE INVENTION

Embodiments of the present invention generally provide improved systems and methods for ocular tomography. These systems and methods can be used to improve the effectiveness of a wide variety of different ophthalmic diagnostic procedures, and various surgical and non-surgical treatments. One embodiment provides a system and method for determining ocular tomography data for the eye using a plenoptic detector. For example, an ocular tomography system can comprise a set of light sources configured to illuminate an eye, a plenoptic detector configured to receive images of the light sources reflected from surfaces of the eye and generate plenoptic image data representing the images, and a processing system coupled to the plenoptic detector. The processing system is configured to analyze the plenoptic image data to determine tomography data for the eye.

In general, the plenoptic detector is configured to capture the intensity, position and direction of light hitting the detector. This information can be used to effectively refocus a plenoptic image at different focus depths after the image has been taken. The processing system can then use such a process to extract depth information from the plenoptic image. For example, by calculating distances between images reflected from different eye surfaces. From this, the processing system determines tomography data for the eye.

In one specific example, the set of light sources are configured to generate Purkinje images from different surfaces in the eye, and the processing system is configured to determine tomography data by calculating distances between the Purkinje images. Such tomography data can then be used for the diagnosis and treatment of a variety of ophthalmic conditions.

In another embodiment, the ocular tomography system includes a set of light sources, a plenoptic detector, and a processing system. In this embodiment the set of light sources is configured to illuminate an eye to generate images on the surfaces of the eye, where the images include a Purkinje I image from light reflected from an outer surface of a cornea in the eye, a Purkinje II image from light reflected from an inner surface of the cornea in the eye, a Purkinje III image from light reflected from an anterior surface of a lens in the eye, and a Purkinje IV image from light reflected from a posterior surface of the lens in the eye.

The plenoptic detector includes a photosensor array comprising a plurality of photosensors and a microlens array comprising a plurality of lenslets. The microlens array is configured to receive images of the light sources reflected from surfaces of the eye and direct the images to the photosensor array. Such an arrangement allows the plenoptic detector to determine both the intensity and the direction of light hitting the detector.

The processing system is coupled to the plenoptic detector to receive plenoptic image data from the plenoptic detector. In one embodiment, the processing system is configured to computationally focus the plenoptic image data at the Purkinje I image, the Purkinje II image, the Purkinje III image, and the Purkinje IV image, and using the computation focusing, to calculate distances between the outer surface of the cornea in the eye, the inner surface of the cornea in the eye, the anterior surface of the lens in the eye, and the posterior surface of the lens in the eye. Again, such tomography data can then be used for the diagnosis and treatment of a variety of ophthalmic conditions.

The above summary and the following detailed description are merely exemplary, illustrative, and explanatory, and are not intended to limit, but to provide further explanation of the invention as claimed. Additional features and advantages of the invention will be set forth in the ensuing detailed descriptions that follow, and in part, will be apparent from the description, or may be learned by practicing various embodiments of the invention. The objectives and other advantages of the invention will be realized by the structures and methods particularly pointed out in the written description and claims as well as the accompanying drawings.

DETAILED DESCRIPTION OF THE INVENTION

The figures and descriptions of the present invention have been simplified to illustrate elements that are relevant for a clear understanding of the present invention, while eliminating, for the purpose of clarity and brevity, many other elements found in typical ophthalmic techniques, systems, methods, lenses, and implantable optic apparatuses. Those of ordinary skill in the art may thus recognize that other elements and/or steps are desirable and/or required in implementing the present invention. However, because such elements and steps are well known in the art, and because they do not necessarily facilitate a better understanding of the present invention, those elements and steps are not discussed. This disclosure is directed to all applicable variations, changes, and modifications known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, brief summary, or the following detailed description.

Embodiments of the present invention generally provide improved systems and methods for ocular tomography. These systems and methods can be used to improve the effectiveness of a wide variety of different ophthalmic diagnostic procedures, and various surgical and non-surgical treatments. One embodiment provides a system and method for determining ocular tomography data for the eye using a plenoptic detector. For example, an ocular tomography system can comprise a set of light sources configured to illuminate an eye, a plenoptic detector configured to receive images of the light sources reflected from surfaces of the eye and generate plenoptic image data representing the images, and a processing system coupled to the plenoptic detector. The processing system is configured to analyze the plenoptic image data to determine tomography data for the eye.

In another embodiment, the ocular tomography system includes a set of light sources, a plenoptic detector, and a processing system. In this embodiment the set of light sources are configured to illuminate an eye to generate images reflected from the surfaces of the eye, where the images include various Purkinje images. The plenoptic detector is configured to capture these Purkinje images and determine both the intensity and direction of light hitting the detector in these images.

Figure 1:
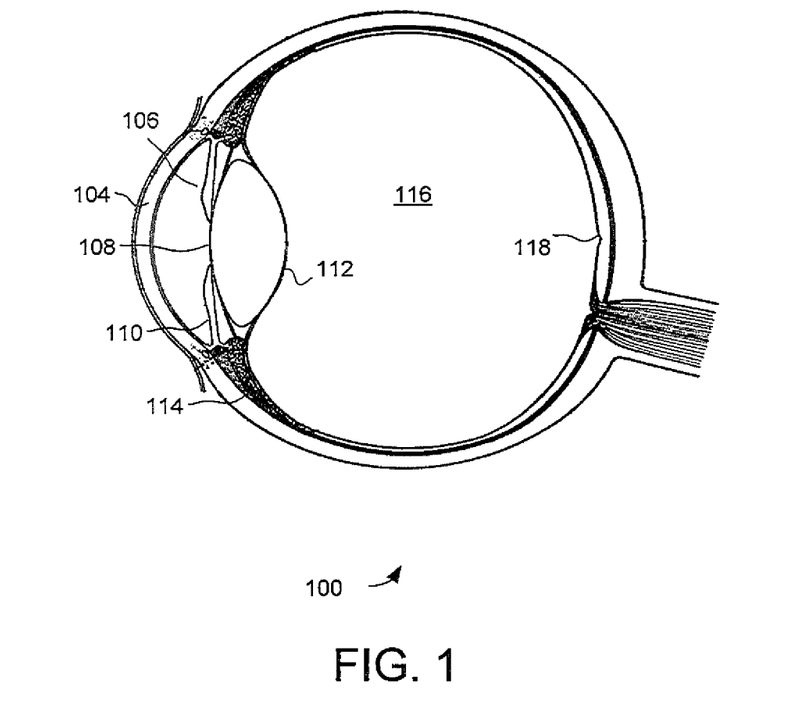
FIG. 1 is a cross-sectional side view of a human eye.

Turning to the drawings, FIG. 1 illustrates a simplified cross-sectional view of an exemplary human eye 100. In general, the eye 100 includes a cornea 104, an anterior chamber 106, a pupil 108, an iris 110, a lens 112, a ciliary muscle 114, a posterior chamber 116, and a retina 118. As briefly described earlier, many modern ophthalmic procedures require accurate measurements of the whole ocular system so that patients may be properly screened and treated. The measurement of the three-dimensional structure of the ocular system is generally referred to as ocular tomography. For example, ocular tomography can include the determination of the thicknesses and/or radii of the cornea 104. As another example, ocular tomography can include the determination of the thicknesses and/or radii of the lens 112. Ocular tomography can also include the determination of the depth of the anterior chamber 106, the distance between the lens 112 and the cornea 104. Ocular tomography can also include the depth of the posterior chamber 116. Each of these various measurements can be useful in diagnosis and treatment, including surgical and non-surgical treatments. Furthermore, improved accuracy and precision of these measurements may lead to enhanced methods for correcting visual defects.

Figure 2:
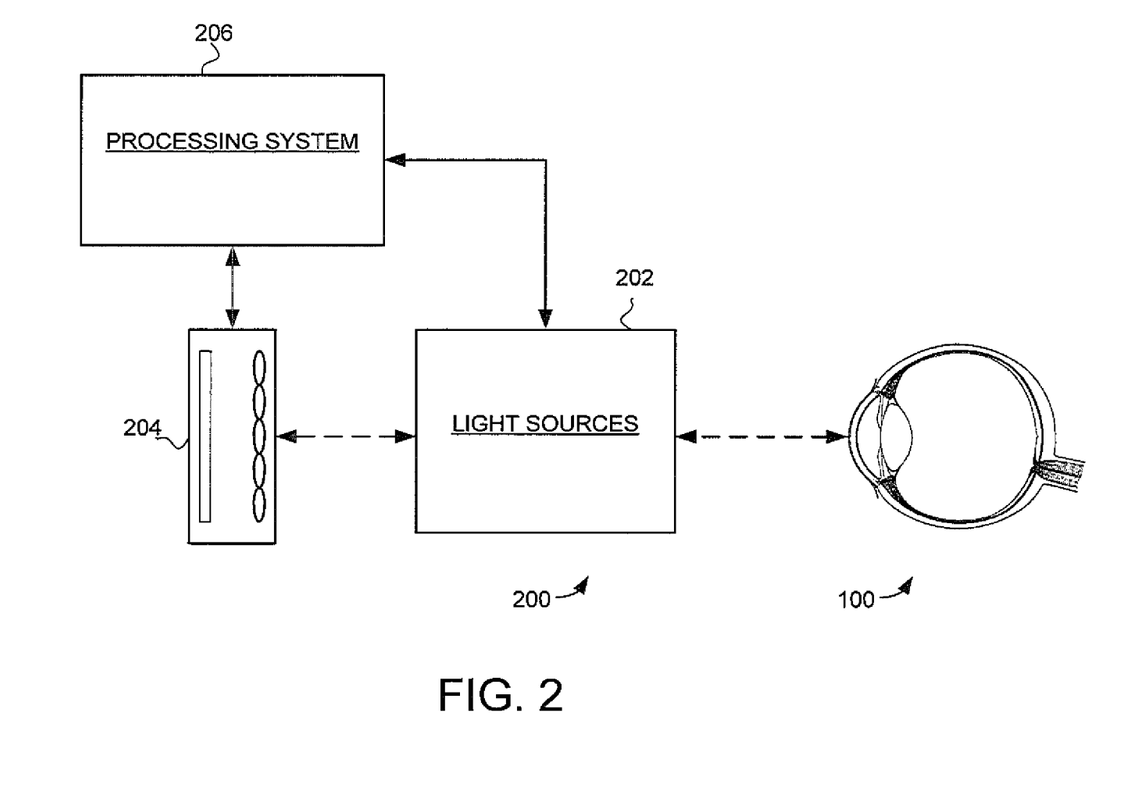
FIG. 2 is a schematic diagram of an ocular tomography system in accordance with an embodiment of the invention.

Turning now to FIG. 2, a simplified schematic view of an ocular tomography system 200 is illustrated. The system 200 includes light sources 202, a plenoptic detector 204, and a processing system 206. In general, the light sources 202 and associated optical elements (not shown in FIG. 2) are configured to illuminate the eye 100 with a set of light sources. For example, the light generator 202 can comprise a set of light emitting diodes (LEDs) configured to illuminate the eye 100. As will be described in greater detail below, other suitable light sources can be used as well. In one specific example, the set of light sources are configured to generate Purkinje images reflected from different surfaces in the eye.

In general, the plenoptic detector 204 is configured to detect the resulting images on the eye 100. Specifically, the plenoptic detector 204 is configured to determine both intensity and direction of light reflecting from the eye 100 and hitting the detector. This information can be used to effectively refocus a plenoptic image at different focus depths after the image has been captured, and this refocusing can be used to extract depth information. For example, by calculating distances between images reflected from different eye surfaces.

As one example implementation, the plenoptic detector 204 can include a photosensor array comprising a plurality of photosensors and a microlens array comprising a plurality of microlenses that are referred to as lenslets. In such a configuration the microlens array is configured to receive images of the light sources 202 reflected from surfaces of the eye 100 and direct the images to the photosensor array. From this, the plenoptic detector 204 can calculate both intensity and direction of light hitting the plenoptic detector 204.

In the embodiment shown in FIG. 2, the light sources 202 and plenoptic detector 204 are each coupled to processing system 206. The processing system 206 is configured to control the light sources 202 and plenoptic detector 204. Additionally, the processing system 206 is configured to analyze the plenoptic image data to determine tomography data for the eye 100. As described above, the plenoptic detector 204 is configured to capture the intensity, position and direction of light hitting the detector. The processing system 206 can use this plenoptic image data to refocus captured images at different focus depths after the images have been taken. The processing system 206 can then use such a process to extract depth information from the plenoptic image. For example, the processing system 206 can be implemented to calculate distances between images reflected from different eye surfaces. From this, the processing system 206 can determine tomography data for the eye.

The light sources 202 can comprise any source of electromagnetic radiation, particularly a source in or near the visible band of the electromagnetic spectrum, for example, in the infrared, near infrared, or ultraviolet bands of the electromagnetic radiation. Furthermore, as used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by a photodetector or electromagnetic image sensor (e.g., CCD) or that is otherwise useful in measuring the optical or physical characteristics of an object under examination.

In one embodiment, the light sources 202 are configured in a pattern that includes a plurality of common elements having a common form and one or more reference elements having a reference form that is different than the common form. As used herein, the term "form", when applied to an element or object, means a shape and orientation of the element or object, without regard to its scale or dimension. As used herein the term "different", when applied to a comparison between two or more "forms", means the forms being compared have a different shape and/or orientation in comparison to one another. As used herein the term "same", when applied to a comparison between two or more "forms", means the forms being compared have equivalent shape and orientation in comparison to one another.

In one embodiment that will be described in greater detail below, the light sources 202 further include a Helmholtz source. The light sources 202 may also include additional light sources that are not generally used for tomography, but may be used for other purpose, for example, to control a pupil size.

In one embodiment the light sources 202 may be configured in a Placido-type source. As used herein, the term "Placido-type source" means a mask, pattern, or plurality of individual light sources disposed such that light from the source reflects off of a reference or test object, passes through an imaging system, and is received by a detector, wherein light from the Placido-type source passes only once through the imaging system. In this embodiment, the individual light sources may be active sources generating light energy or apertures through which light energy is transmitted. Individual mask or pattern features may include lighter or more reflective portions of the mask or pattern configured to reflect light. As used herein, the term "Placido disk" means a Placido-type source configured as a plurality of concentric rings or annular shapes.

In one specific example, the light sources 202 are configured to generate Purkinje images from different surfaces in the eye 100, and the processing system 206 is configured to determine tomography data by calculating distances between the Purkinje images. As more specific examples, the light sources can be arranged in a circle or semicircle, and these Purkinje images can include a Purkinje I image from light reflected from an outer surface of a cornea in the eye 100, a Purkinje II image from light reflected from an inner surface of the cornea in the eye 100, a Purkinje III image from light reflected from an anterior surface of a lens in the eye 100, and a Purkinje IV image from light reflected from a posterior surface of the lens in the eye 100.

In this embodiment, the plenoptic detector 204 captures these four Purkinje images in the plenoptic image data, and the processing system 206 is configured to determine the distances between the surfaces these Purkinje images are reflected from. For example, the processing system 206 can be configured to computationally focus the plenoptic image data at the Purkinje I image, the Purkinje II image, the Purkinje III image, and the Purkinje IV image, and using the computational focusing, to calculate distances between the outer surface of the cornea in the eye 100, the inner surface of the cornea in the eye 100, the anterior surface of a lens in the eye 100, and the posterior surface of the lens in the eye 100. Similar procedures can be used to calculate various radii in the eye 100, including both the inner and outer radii of the cornea and the inner and outer radii of the lens.

To facilitate these actions the processing system 206 can comprise any suitable configuration of processing elements, including various computer memories, controllers, and other devices. For example, the processing system 206 can be implemented as software residing in memory and being executed by a processor, or as hardware hardcoded into a processing device, or any combination thereof.

The system 200 can be implemented as a stand-alone device or as part of a larger diagnostic system or a larger ophthalmic laser system. For example, the system 200 can be implemented as part of an ophthalmic diagnostic and/or measurement system designed to provide one or more of wavefront aberrometry, topography, autorefractometry, pupillometry, and optical coherence tomography. More specifically, the system 200 may be incorporated into and implemented as part of the WaveScan® System or the iDesign Advanced WaveScan Studio® System, both produced by Abbott Medical Optics Inc. These ophthalmic diagnostic and measurement systems use a Shack-Hartmann wavefront sensor to quantify aberrations throughout the entire optical system of the patient's eye, including second-order aberrations related to spherical error and cylindrical errors and higher order aberrations related to coma, trefoil, and spherical aberrations. An exemplary wavefront diagnostic system is described in U.S. Pat. No. 7,931,371, issued to Dai, which is incorporated by reference in its entirety. In one embodiment, the system 200 may be incorporated into and implemented as part of a device or system that is used to generate pulsed laser beams, including non-ultraviolet (non-UV), ultrashort pulsed laser beams that have pulse durations that are measured in femtoseconds, as described in U.S. Pat. Nos. 4,764,930 and 5,993,438. Certain non-UV, ultrashort pulsed laser systems are used for ophthalmic surgeries. For example, U.S. Pat. No. 5,993,438 discloses a laser device for performing ophthalmic surgical procedures to effect high-accuracy corrections of optical aberrations. In another embodiment, the system 200 may be incorporated into and implemented as part of a UV based laser system. Further details of suitable UV systems for performing laser ophthalmic procedures can be found in commonly-assigned U.S. Pat. Nos. 4,665,913, 4,669,466, 4,732,148, 4,770,172, 4,773,414, 5,207,668, 5,108,388, 5,219,343, 5,646,791 and 5,163,934.

Figure 3:
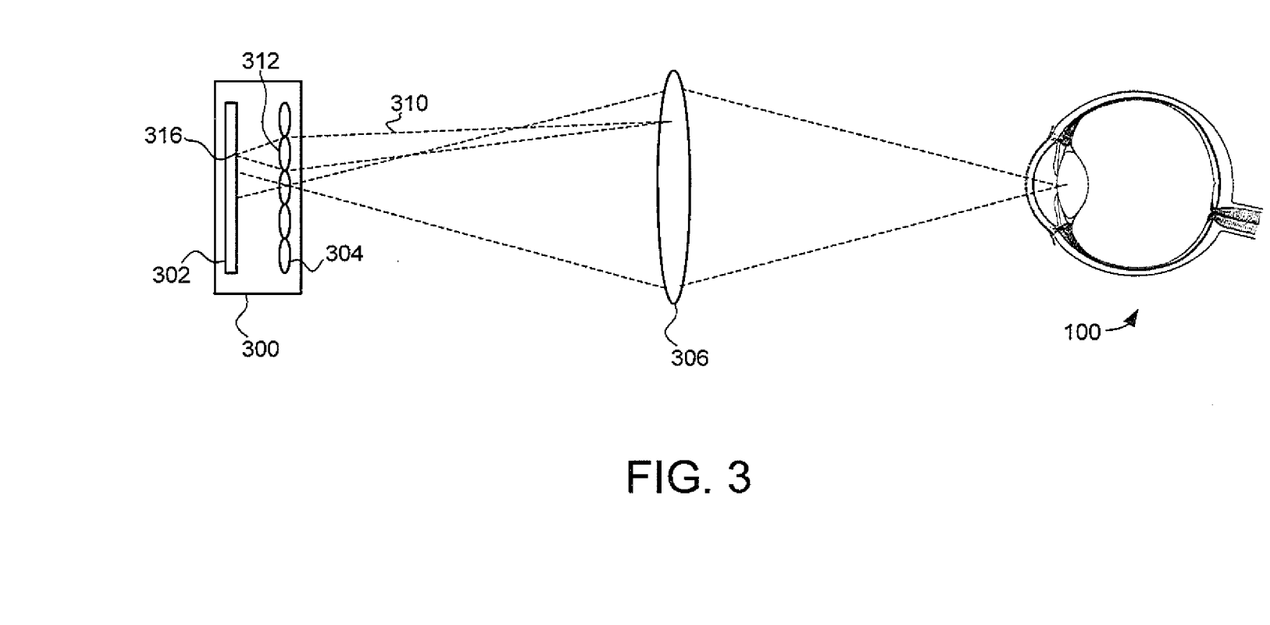
FIG. 3 is a schematic diagram of a plenoptic detector and eye in accordance with an embodiment of the invention.

Turning now to FIG. 3, a plenoptic detector 300 is illustrated schematically. The plenoptic detector 300 includes a photosensor array 302 comprising a plurality of photosensors and a microlens array 304 comprising a plurality of microlenses, with individual microlenses sometimes referred to as lenslets. In the illustrated embodiment, the microlens array 304 is configured to receive images of the light sources (not shown in FIG. 3) reflected from surfaces of the eye 100 and directed to the detector 300 with lens 306. In general, each lenslet in the microlens array 304 covers multiple sensors or "pixels" in the photosensor array 302. As will be described in greater detail below, this results in reduced spatial resolution, but also provides the ability to determine direction information for incident light hitting the plenoptic detector 300.

A variety of different types of devices can be used for the photosensor array 302 in the plenoptic detector 300. For example, the individual photosensors can be implemented with digital imaging devices such as a charge coupled detector (CCD). As another example, the photosensors can be implemented with active pixel sensors. Likewise, the microlens array can be implemented in a variety of different ways. For example, the microlens array can be manufactured by photolithographic or molding processes. Furthermore, different relative positioning between the various elements can be used. For example, in some plenoptic detectors 300 the microlens array 304 is positioned to be in the image plane of the main lens 306. Conversely, in other examples the microlens array 304 is positioned to be in front of or behind the image plane of the main lens 306. Likewise, different relative positioning between the microlens array 304 and the photosensor array 302 can be used. For example, the photosensor array 302 may be positioned one lenslet focal length behind the microlens array 304.

Next, it should be noted that because each lenslet in microlens array 304 covers multiple pixels in the photosensor array 302, the resulting images captured by the photosensor effectively have reduced spatial image resolution, while adding the ability to determine directional information. As one example, each lenslet in the microlens array 304 may correspond to 100 pixels in the photosensor array 302. In such an embodiment the resulting images would be reduced in spatial resolution by two orders of magnitude. Again, this is just one example, and in other cases each lenslet could correspond to more or less pixels on the photosensor array 302. For example, some plenoptic detectors 300 may use 10 pixels per lenslet in the microlens array 302, and would thus have less reduction in resolution. However, such plenoptic detectors 300 would also provide reduced directional information. And while the reduction in resolution may be considered undesirable for some applications, the embodiments describe herein use such plenoptic image data to determine information about an eye that could not be determined with an ordinary camera regardless of the increased resolution.

In general, the plenoptic detector 300 as illustrated in FIG. 3 is configured to determine both intensity and direction of light reflecting from the eye 100 and hitting the detector 300. To accomplish this, the lens 306 is configured to direct light reflected from surfaces of the eye 100 to the microlens array 304. The microlens array 304 is configured to receive this light and direct that light to the photosensor array 302. From this, the plenoptic detector 300 can calculate both the intensity and direction of the light reflected from the eye 100.

In general, each lenslet in the microlens array 304 receives light from the eye at a different angle than the other lenslets in the array, and each photosensor in the photosensor array 302 receives a different view of the eye from each lenslet in the array of microlenses 304, and wherein each different view of the eye is received at a separate location on the photosensor array 302 to produce a multidimensional array of different views of the eye at the photosensor array 302. Stated another way, each lenslet in the microlens array 304 receives light from the eye at different angles and spatially separates the light at different angles at the photosensor array 302. Stated another way, wherein each lenslet in the microlens array 304 is configured such that light arriving at a point in different directions is directed at a different point on the photosensor array 302 such that direction information for light ray can be determined from a position of the light ray Conventional cameras capture two-dimensional images, with each pixel in the image representing the total amount of light striking each point in the camera sensor. Notably, a conventional two-dimensional image does not include any information about the direction any of the light was traveling when it hit the sensor. In contrast, a plenoptic detector such as detector 300 captures information on the directional distribution of the light rays.

Specifically, the microlens array 304 enables the plenoptic detector 300 to capture the light-field, i.e. to record not only image intensity, but also the distribution of intensity in different directions at each point. Specifically, the rays at the microlens array 304 have different angles, and passing though a lenslet causes rays with different angles to separate. Thus, each lenslet in the microlens array 304 splits a beam coming to it from the main lens 306 into different rays, and each of these different rays hits a different pixel on photosensor array 302. The result is a multipixel image formed under each lenslet in the microlens array 304, with the multipixel image containing measurements of different angular samples of the incident light at the lenslet. This multipixel area under each lens may be referred to as a "macropixel", and the plenoptic detector 300 effectively generates a "microimage" at each such macropixel. For example, a plenoptic detector with 100,000 lenslets in the microlens array 304 will contain 100,000 macropixels, and thus generate 100,000 microimages.

An example of this is illustrated in FIG. 3, which shows rays 310 hitting lenslet 312 in microlens array 304, and subsequently hitting a point 316 on photosensor array 302. For clarity, only rays through lenslet 312 are illustrated, but other rays through different lenslets would also fall at different pixels on the photosensor array 302. The result is a microimage at each macropixel, and the raw image data of the plenoptic detector 300 could thus be considered an array of such microimages.

Stated another way, each lenslet in the microlens array 304 functions to convert directional or angular information into positional information that is captured at the photosensor array 302. Because of this conversion, the position of a ray at the photosensor array 302 provides directional or angular information about the ray. Thus, the measurements taken at the pixels in the photosensor array 302 can be used to provide both directional and intensity data regarding light reflected from the eye 100. And such measurements, as a set of such plenoptic image data, can be used form an image by selecting appropriate pixels from each microimage. Furthermore, by mixing pixels from different microimages images at different focus depths that can be generated.

Figure 4:
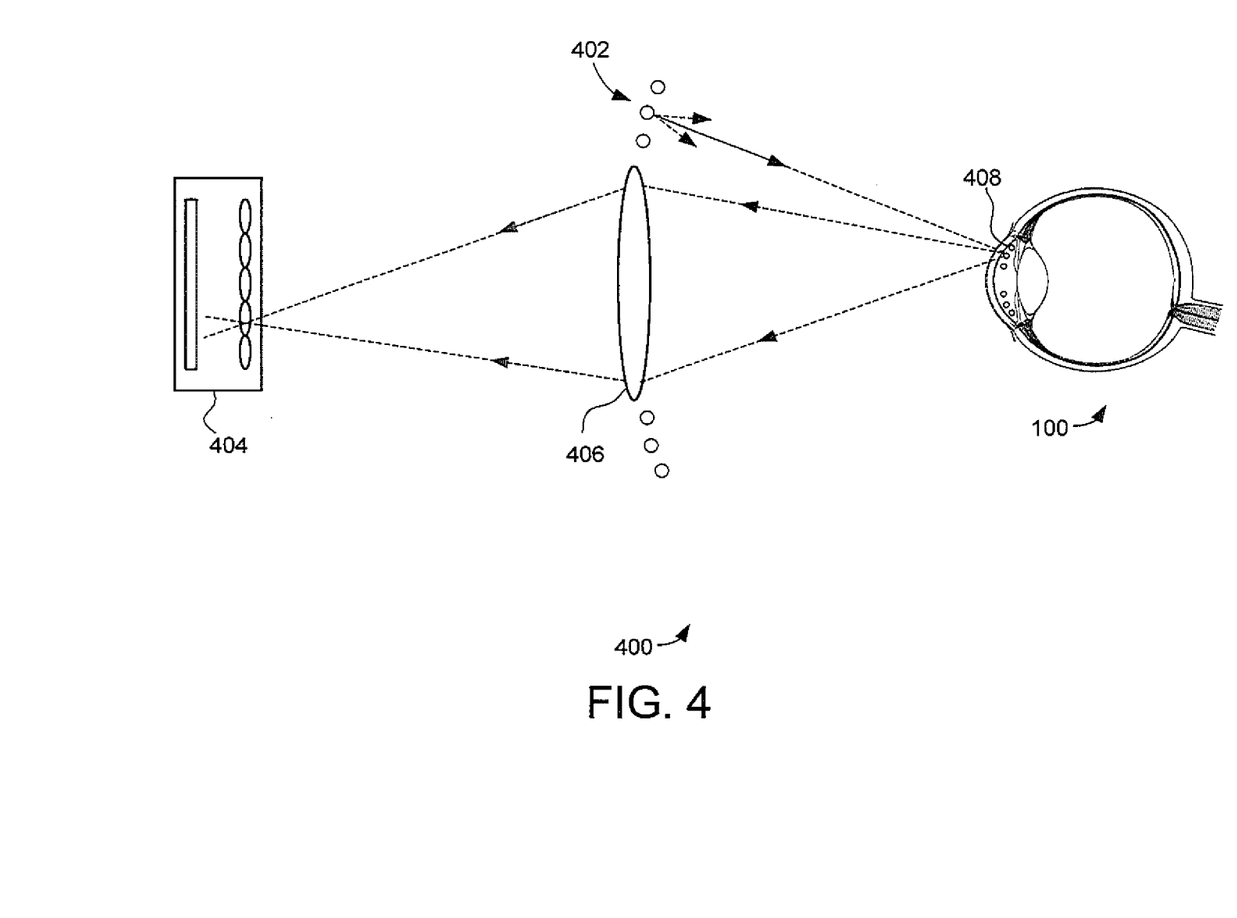
FIG. 4 is a schematic diagram of an ocular tomography system in accordance with an embodiment of the invention.

Turning now to FIG. 4, a simplified schematic view of an ocular tomography system 400 is illustrated. The system 400 includes light sources 402, a plenoptic detector 404, and a lens 406. Not shown is a processing system that would be coupled to at least the plenoptic detector 404. In general, the light sources 402 and the lens 406 are configured to illuminate the eye 100. In this case the light sources 402 can comprise light emitting diodes (LEDs) or other such light sources arranged in a semicircle and configured to illuminate the eye 100 to generate Purkinje images 408 on different surfaces in the eye.

In general, the plenoptic detector 404 is configured to detect the resulting Purkinje images 408 on the eye 100. Specifically, the plenoptic detector 404 is configured to measure both intensity and direction of light reflecting from the eye 100 and hitting the detector 404. The plenoptic image data can then be processed to refocus the reflected light at the different focus depths that correspond to different Purkinje images and different positions on those images. This refocusing can be used to extract depth information, specifically to calculate the shapes of the Purkinje images 408 and/or distance between Purkinje images 408. From this, the processing system can determine tomography data for the eye.

As more specific examples, the Purkinje images 408 can include a Purkinje I image from light reflected from an outer surface of the cornea in the eye 100, a Purkinje II image from light reflected from an inner surface of the cornea in the eye 100, a Purkinje III image from light reflected from an anterior surface of the lens in the eye 100, and a Purkinje IV image from light reflected from a posterior surface of the lens in the eye 100.

Figure 5:
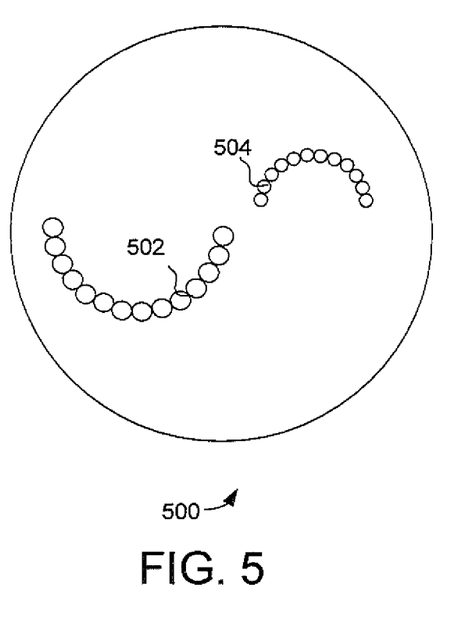
FIG. 5 is a front portion view of an eye with images formed in accordance with an embodiment of the invention.

Turning briefly to FIG. 5, a front portion view of an eye 500 is illustrated. According to the techniques described in this application, the view of eye 500 also illustrates a first image 502 of light sources reflected from an anterior surface of lens (not shown in FIG. 5) and a second image 504 of light sources reflected from a posterior surface of lens. In this specific embodiment, the first image 502 reflected from an anterior surface of the lens comprises a portion of a Purkinje III circle, and the second image 504 reflected from a posterior surface of the lens comprises a portion of a Purkinje IV circle. Both the Purkinje III circle and Purkinje IV circle are illustrated as a collection of smaller circles, wherein each smaller circle represents the effect of one light source 402 of FIG. 4.

Returning to FIG. 4, the plenoptic detector 404 captures plenoptic image data that includes one or more of such Purkinje images. In one embodiment, the processing system is configured to determine the distances between the surfaces these Purkinje images are reflected from. For example, the processing system can be configured to computationally focus the plenoptic image data at the Purkinje I image, the Purkinje II image, the Purkinje III image, and the Purkinje IV image, and using the computational focusing, to calculate distances between the outer surface of the cornea in the eye 100, the inner surface of the cornea in the eye 100, the anterior surface of the lens in the eye 100, and the posterior surface of the lens in the eye 100. For example, the processing system can computationally focus the Purkinje III image, and thus determine the parameters that result in the Purkinje III image being focused. Then, the processing system can computationally focus the Purkinje IV image, and thus determine the parameters that result in the Purkinje IV image being focused. Then from these parameters the processing system can determine the depth of the focused images, and thus the distances between the focused images. Because the focused Purkinje III image corresponds to light reflected from an anterior surface of the lens, and the Purkinje IV image corresponds to light reflected from a posterior surface of the lens, the distance between focus images corresponds to the thickness of the lens as well as the curvatures of the surfaces. Similar procedures can be used with the other Purkinje images to determine other tomography parameters in the eye. For example, to determine the thickness of the cornea, the depth of the anterior chamber, the distance between the lens and the cornea, etc.

Furthermore, similar procedures can be used to determine various radii of curvature in the eye. For example, by the determining how the focus parameters change at different positions along the Purkinje images the radius of curvature of the associated surfaces can be determined. Thus, both the inner and outer radii of the cornea and the inner and outer radii of the lens can be determined.

Figure 6:
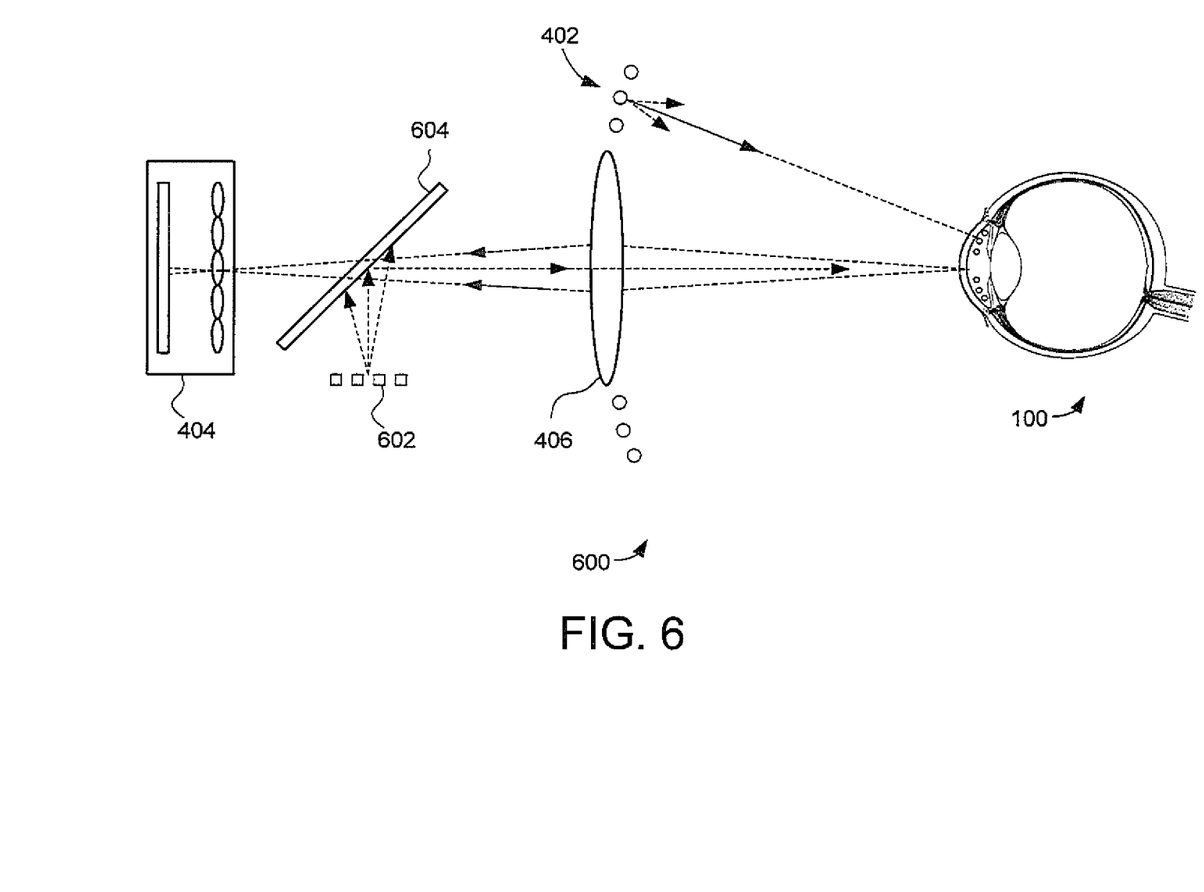
FIG. 6 is a schematic diagram of an ocular tomography system in accordance with an embodiment of the invention.

Turning now to FIG. 6, a simplified schematic view of an ocular tomography system 600 is illustrated. The system 600 is similar to system 400 with the addition of a Helmholtz light source 602 and beam splitter 604. In general, the Helmholtz light source 602 is used to provide better measurements of ocular tomography near the center of the eye 100. As one example, the Helmholtz light source 602 comprises a plurality of second elements or light sources that are optically located at a distance from the lens 406 that is equal to one focal length of the lens 406. The Helmholtz light source 602 can comprise any source of electromagnetic radiation. The Helmholtz light source 602 is configured to reflect light off a beam splitter 604, and then to transmit the reflected light through the lens 406 and off a surface of the eye 100. The light reflected from a surface of the eye is passed back to the plenoptic detector 404. As more detailed examples, the Helmholtz light source 602 can comprise a plurality of individual light sources (e.g., LED light sources), a plurality of apertures in an opaque mask that is opaque mask that is illuminated from behind the mask, or the like. As one example, the Helmholtz light source 602 can include a plurality of Helmholtz common elements having a common form and a Helmholtz reference element that is different than the common form.

As used herein, the term "Helmholtz source" or "Helmholtz light source" means one or a plurality of individual sources or individual light sources disposed such that light from each of the individual light sources passes through an optical element having optical power, reflects off of a test object, passes through the optical element, and is received by a detector, such as the plenoptic detector 404. In general, it is a characteristic of Helmholtz sources that the signal at the detector is independent of the position of the test object relative to the Helmholtz source.

The beam splitter 604 is configured to reflect light from the Helmholtz light source 602 through the lens 406 and to the eye 100. Like the light from the light sources 402, the light from Helmholtz light source 602 forms images from the surfaces of the eye that are reflected back through the beam splitter 604 to the plenoptic detector 404. In this embodiment the Helmholtz light source 602 is used to provide more accurate measurements of ocular tomography for portions of the eye 100 near the center. Specifically, because of their position, the light sources 402 may be limited in ability to form images on surfaces in the center portions of the eye, and thus the accuracy of the tomography based on those images may be limited for the center portions of the eye 100. Thus, the addition of the Helmholtz light source 602 and beam splitter 604 may provide more complete tomography of the eye.

To facilitate determining ocular tomography using the images formed by the Helmholtz light source 602, the processing system can again computationally focus the various images created by the Helmholtz light source 602 and thus determine the parameters that result in these images being focused. Then from these parameters the processing system can determine the virtual depth of the focused images and thus the distances between the focused images. Like the Purkinje images discussed above, these calculations can be used as inputs to additional calculations determine the distances between surfaces in the eye and/or the radii or curvatures of the various surfaces.

The embodiments described herein thus provide techniques for accurate determination of ocular tomography. Such techniques can be used for any ophthalmic procedure requiring accurate determinations. These techniques can thus be used to improve the effectiveness of a wide variety of different ophthalmic procedures.

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. An ocular tomography system, the ocular tomography system comprising:
   a set of light sources configured to illuminate an eye which includes a cornea and a lens;
   a plenoptic detector configured to receive images of the light sources reflected from surfaces of the cornea and lens of the eye and to generate plenoptic image data representing the images;
   a processing system coupled to the plenoptic detector, wherein the processing system is configured to analyze the plenoptic image data to determine tomography data for the eye by computationally focusing at least two different Purkinje images included the plenoptic image data, by determining corresponding depths of the two different computationally focused Purkinje images in the plenoptic image data, and by calculating from the depths of the two different computationally focused Purkinje images a distance between two surfaces of the eye selected from an outer surface of the cornea, an inner surface of the cornea, an anterior surface of the lens, and a posterior surface of the lens.

2. The system of claim 1 wherein the plenoptic detector comprises:
a photosensor array, the photosensor array comprising a plurality of photosensors; and
a microlens array, the microlens array comprising a plurality of lenslets configured to direct the images to the photosensor array, the microlens array arranged a predetermined distance from the photosensor array.

3. The system of claim 2 wherein the photosensor array comprises a two dimensional array of photosensors, and wherein the microlens array comprises a two dimensional array of lenslets.

4. The system of claim 2 wherein the photosensor array is arranged in an image plane.

5. The system of claim 2 wherein each lenslet in the microlens array receives light from the eye at different angles and spatially separates the light at different angles at the photosensor array.

6. The system of claim 3 wherein each lenslet in the microlens array is configured to split a light beam received by it into different rays, wherein each of the different rays is directed to a different photosensor of the photosensor array such that a multipixel microimage is formed under each lenslet in the microlens array.

7. The system of claim 6 wherein the processing system is configured to computationally focus each of the at least two different Purkinje images by selecting outputs of photosensors from each of the microimages and combining the selected photosensor outputs.

8. The system of claim 1 wherein the set of light sources is configured to generate a Purkinje I image from light reflected from an outer surface of a cornea in the eye, generate a Purkinje II image from light reflected from an inner surface of the cornea in the eye, generate a Purkinje III image from light reflected from an anterior surface of a lens in the eye, and generate a Purkinje IV image from light reflected from a posterior surface of the lens in the eye; and wherein the processing system is configured to analyze the plenoptic image data to determine tomography data for the eye by calculating a distance between the Purkinje I image and the Purkinje II image, calculating a distance between the Purkinje II image and the Purkinje III image, and calculating a distance between the Purkinje III image and the Purkinje IV image.

9. An ocular tomography system, the ocular tomography system comprising:
a set of light sources configured to illuminate an eye to generate images from the surfaces of the eye, the images including a Purkinje I image from light reflected from an outer surface of a cornea in the eye, a Purkinje II image from light reflected from an inner surface of the cornea in the eye, a Purkinje III image from light reflected from an anterior surface of a lens in the eye, and a Purkinje IV image from light reflected from a posterior surface of the lens in the eye;
a plenoptic detector, the plenoptic detector including:
a photosensor array, the photosensor array comprising a plurality of photosensors; and
a microlens array, the microlens array comprising a plurality of lenslets configured to receive images of the light sources reflected from surfaces of the eye and direct the images to the photosensor array, the microlens array arranged a predetermined distance from the photosensor array, wherein the photosensor array is configured to generate plenoptic image data representing the images;
a processing system coupled to the plenoptic detector, the processing system configured to:
receive the plenoptic image data;
computationally focus the plenoptic image data at the Purkinje I image, the Purkinje II image, the Purkinje III image, and the Purkinje IV image; and
use focus parameters which computationally focus the plenoptic image data at the Purkinje I image, the Purkinje II image, the Purkinje III image, and the Purkinje IV image to calculate distances between the outer surface of the cornea in the eye, the inner surface of the cornea in the eye, the anterior surface of a lens in the eye, and the posterior surface of the lens in the eye.

10. A method for determining ocular tomography, the method comprising:
illuminating an eye using a set of light sources;
receiving images of the light sources reflected from surfaces of the eye at a plenoptic detector configured and generating plenoptic image data representing the images; and
analyzing the plenoptic image data to determine tomography data for the eye by:
computationally focusing at least two different Purkinje images included the plenoptic image data,
determining corresponding depths of the two different computationally focused Purkinje images in the plenoptic image data, and
calculating from the depths of the two different computationally focused Purkinje images a distance between two surfaces of the eye selected from an outer surface of the cornea, an inner surface of the cornea, an anterior surface of the lens, and a posterior surface of the lens.

11. The method of claim 10 wherein the plenoptic detector comprises:
a photosensor array, the photosensor array comprising a plurality of photosensors; and
a microlens array, the microlens array comprising a plurality of lenslets configured to direct the images to the photosensor array, the microlens array arranged a predetermined distance from the photosensor array.

12. The method of claim 11 wherein the photosensor array comprises a two dimensional array of photosensors, and wherein the microlens array comprises a two dimensional array of lenslets.

13. The method of claim 11 wherein each lenslet in the microlens array receives light from the eye at different angles and spatially separates the light at different angles at the photosensor array.

14. The method of claim 11 wherein each lenslet in the microlens array splits a light beam received by it into different rays, and directs each of the different rays to a different photosensor of the photosensor array such that a multipixel microimage is formed under each lenslet in the microlens array.

15. The method of claim 10 wherein computationally focusing each of the at least two different Purkinje images comprises:
selecting outputs of photosensors from each of the microimages, and
combining the selected photosensor outputs.

16. The method of claim 10 wherein the set of light sources is configured to generate a Purkinje I image from light reflected from an outer surface of a cornea in the eye, generate a Purkinje II image from light reflected from an inner surface of the cornea in the eye, generate a Purkinje III image from light reflected from an anterior surface of a lens in the eye, and generate a Purkinje IV image from light reflected from a posterior surface of the lens in the eye; and wherein the analyzing the plenoptic image data to determine tomography data for the eye comprises calculating a distance between the Purkinje I image and the Purkinje II image, calculating a distance between the Purkinje II image and the Purkinje III image, and calculating a distance between the Purkinje III image and the Purkinje IV image.

* * * * *